United States Patent [19]

Gebski et al.

[11] Patent Number: 5,783,400
[45] Date of Patent: Jul. 21, 1998

[54] METHOD FOR THE ISOLATION OF LIPOPROTEIN ALLOWING FOR THE SUBSEQUENT QUANTIFICATION OF ITS MASS AND CHOLESTEROL CONTENT

[75] Inventors: Christine P. Gebski, Bradford; C. William Christopher, Rockport; James F. Ollington, Chelmsford, all of Mass.

[73] Assignee: Genzyme Corporation, Cambridge, Mass.

[21] Appl. No.: 479,700

[22] Filed: Jun. 7, 1995

Related U.S. Application Data

[63] Continuation-in-part of Ser. No. 393,337, Feb. 23, 1995, which is a continuation of Ser. No. 515,596, Apr. 27, 1990, Pat. No. 5,403,745, and a continuation-in-part of Ser. No. 198,919, Feb. 18, 1994, and Ser. No. 198,430, Feb. 22, 1994.

[51] Int. Cl.$^6$ .................. C12Q 1/60; G01N 33/573
[52] U.S. Cl. .................. 435/7.4; 424/130.1; 435/11; 435/962; 436/175; 436/178; 436/501; 436/518; 436/536; 436/824; 436/825
[58] Field of Search .................. 435/7.4, 11, 962; 436/175, 536, 501, 825, 824, 518, 177, 178; 424/130.1

[56] References Cited

U.S. PATENT DOCUMENTS

| 4,244,694 | 1/1981 | Farina et al. ............... 23/230 B |
| 4,366,244 | 12/1982 | Pascal ............... 435/11 |
| 4,746,605 | 5/1988 | Kerscher et al. ............... 435/7 |
| 4,945,040 | 7/1990 | Fless et al. . |
| 5,229,073 | 7/1993 | Luo et al. . |
| 5,320,968 | 6/1994 | Seman ............... 436/71 |
| 5,403,745 | 4/1995 | Ollington et al. ............... 435/11 |

FOREIGN PATENT DOCUMENTS

| 0 141 343 | 5/1989 | European Pat. Off. . |
| 0 327 418 | 8/1989 | European Pat. Off. . |
| 0 415 298 | 3/1991 | European Pat. Off. . |
| 506523 | 9/1992 | European Pat. Off. . |
| 621284 | 10/1994 | European Pat. Off. . |
| 650055 | 4/1995 | European Pat. Off. . |
| 659765 | 6/1995 | European Pat. Off. . |
| 9209893 | 6/1992 | WIPO . |
| 9221015 | 11/1992 | WIPO . |
| 93/12429 | 6/1993 | WIPO . |

OTHER PUBLICATIONS

Medline Abstract No. 93043129., 1992.
Berg, *Acta Pathol. Microbiol. Scand.*, 59:369–382., 1963.
Schaefer et al., *NEJM* 312:1300–1310., 1985.
Gaubatz, et al., *Methods in Enzymology* 129:167–186., 1986.
McNamara et al., *Clinica Chimica Acta* 166:1–8., 1987.
N.I.H. Publication No. 88–2925., 1988.
Utermann, *Hum. Genet.* 78:41–46., 1988.
Gaubatz, *J. Lipid Res.* 31:603–613., 1990.
Craig, *Appl. Theor. Electrophoresis* 2:135–140., 1991.
Marcovina, *Biochem. Biophys. Res. Comm.* 191:1192–1196.,1993.
Karmansky, *Clin. Biochem.* 27:151–162., 1994.
Leerink, *Fibrinolysis* 8:214–220., 1994.
Seman et al., *Clin. Chem.* 40:400–403., 1994.
Kulkarni et al., *J. Lipid Research* 35:159–168., 1994.
Campos et al., *Clinica Chimica Acta* 230:43–50., 1994.
Nauck et al., *Clin. Chem.* 41:731–738., 1995.

*Primary Examiner*—James C. Housel
*Assistant Examiner*—Rodney P. Swartz
*Attorney, Agent, or Firm*—Bromberg & Sunstein LLP

[57] ABSTRACT

A method is provided for preparing lipoprotein (a) from a volume of biological fluid that is substantially free of lipoproteins of another class. The method involves an ultracentrifugation step in which at least one fraction is recovered that contains Lp(a). This material is then reacted with immobilized ligand to remove non-Lp(a) interfering substances from the fraction, the Lp(a) remaining unbound. The non-reacted Lp(a) is subsequently obtained in a form that is suitable for use in the analysis of any of protein concentration, protein isoform determination or cholesterol assays. A method of identifying and measuring an amount of one or more isoforms of Lp(a) is further provided.

25 Claims, 6 Drawing Sheets

METHOD FOR THE ISOLATION OF LIPOPROTEIN ALLOWING FOR THE SUBSEQUENT QUANTIFICATION OF ITS MASS AND CHOLESTEROL CONTENT

CROSS REFERENCE

This application is a continuation-in-part of application Ser. No. 08/393,337, filed Feb. 23, 1995, which is a continuation of application Ser. No. 07/515,596, filed Apr. 27, 1990, now U.S. Pat. No. 5,403,745. This application is also a continuation-in-part of application Ser. No. 08/198,919, filed Feb. 18, 1994, and application Ser. No. 08/198,430, filed Feb. 22, 1994. All parent applications and issued patents are herein incorporated by reference.

TECHNICAL FIELD

The present invention relates to a composition and methods of preparing reference standards for Lp(a) assays and methods for obtaining unbiased quantitative data on Lp(a) in clinical samples.

BACKGROUND OF THE INVENTION

Triglycerides and cholesterol are transported in the blood via lipoprotein particles. Abnormalities in these lipoproteins, either inherited, environmentally contributed, or a combination of both, lead to a variety of disorders including a predisposition to premature coronary heart disease (CHD) and atherosclerosis (*N.I.H Publication Number* 88-2925 (1988); and Schaefer et al., *NEJM* 312:1300–1310 (1985)).

Lipoprotein particles are divided into four major classes based on their density, composition, and electrophoretic mobility: The classes are chylomicrons, very low density lipoproteins (VLDL), low density lipoproteins (LDL) and high density lipoproteins (HDL). LDL and HDL particles may be further subdivided on the basis of their hydrated densities. The lipoprotein particles are composed of triglycerides, cholesterol, fatty acids esters of cholesterol, phospholipid and protein. The varying ratios of protein to lipid, in different lipoprotein classes, account for the physical differences by which these particles can be fractionated by density gradient centrifugation.

The protein components, known as apolipoproteins, are responsible for a variety of cellular functions. Increased levels of LDL cholesterol and decreased levels of HDL cholesterol have been shown to be risk factors for CHD. Consequently, clinical diagnostic assays for cholesterol content in the major lipoprotein classes are performed extensively and a large body of statistical data on the normal ranges for these classes is available and is standardized by the Centers for Disease Control (McNamara et al., *Clinica Chimica Acta* 166:1–8 (1987)).

In 1963, Berg described a class of lipoprotein named lipoprotein(a) abbreviated Lp(a)(Berg, *Acta Pathol. Microbiol. Scand.*, 59:369–382 (1963)) that appeared to be associated with coronary heart disease in men and as such might be an important cholesterol-containing blood constituent.

The structure and possible biological role of Lp(a) has been recently reviewed (Karmansky, *Clin. Biochem.* 27:151–162 (1994)). Briefly, the Lp(a) molecule is an LDL-like, apolipoprotein $B_{100}$—containing moiety with an additional large molecular weight glycoprotein known as apolipoprotein(a). According to FIG. 1, cholesterol (1) comprises about 25% of the total mass of Lp(a). The lipoprotein particle also contains small amounts of triglyceride and lipid as well as the glycoproteins-apolipoprotein $B_{100}$ (apo $B_{100}$) (2) and apolipoprotein (a) (apo (a))(7). In fact, apo(a) accounts for 8–12% of total mass of Lp(a). The apo (a) portion of the molecule is linked to the surface apo $B_{100}$ of the LDL particle by disulfide bond(s) and as such can be readily disrupted during handling of the particles.

Apo(a) is composed of a variable number of kringle 4 domains (5), which exhibit 75–85% homology with plasminogen kringle 4 domain, a kringle 5 domain (4) and a protease domain (3). At least thirty four different apo(a) isoforms have been identified (Utermann, *Hum. Genet.*, 78:41–46 (1988) and Marcovina, *Biochem. Biophys. Res. Comm.* 191:1192–1196 (1993)). These isoforms vary according to the number of kringle 4 domains in the protein and according to the amount of oligosaccharide (6) which is attached to apo(a). This variation is reflected in the substantial size variation in apo(a) that is observed. (Apo(a) ranges in size from 240 to 800 kilodaltons (kDa) depending on the number of kringle 4 domains.)

The epidemiological data supporting the link between Lp(a) and coronary heart disease is fragmentary in part because of a lack of a standardized reference sample of Lp(a) for use during routine assays on mass and cholesterol content of Lp(a) in clinical samples. There is currently no assay available for routinely identifying the isoforms of Lp(a) in clinical samples and therefore it is unknown whether any particular isoform or mix of isoforms carries a larger risk for the patient in developing CHD.

Because of the lack of availability of standardized reference preparations of Lp(a) for use during performance of assays in different laboratories, it has not been possible to effectively monitor interlaboratory, interassay or intraassay variability.

Not only is the overall consistency of clinical testing for Lp(a) affected by the lack of a standardized reference preparation, it is also probable that current methods for preparing clinical samples for testing for Lp(a) give rise to a bias in measuring certain isoforms of Lp(a). For example, the method described by Seman et al., *Clin. Chem.* 40:400–403 (1994), isolates Lp(a) from clinical samples by selectively binding Lp(a) to a lectin column and washing away the non-reacting substances. Subsequently, the Lp(a) is eluted away from the lectin and assayed by measuring cholesterol content. It is possible that those isoforms that have larger numbers of kringle 4 domains will absorb to the lectin more readily than those Lp(a) isoforms of lower molecular weight. It would be desirable to develop a method that does not carry the inherent risk of bias toward one group of isoforms of Lp(a). Once the Lp(a) is removed from other cholesterol carrying lipoproteins, a cholesterol assay can be used to obtain a measure of the amount of Lp(a) in the sample.

An alternate method of assaying Lp(a) is by performing an ELISA test using antibodies to Lp(a). These tests are sold commercially by several suppliers for research purposes only. Traditionally, anti-apo(a) antibodies have been used in these tests. The disadvantage of using apo(a) to measure the amount of Lp(a) in a clinical sample is that if the antibody binds to kringle 4, the predominant surface antigen, the signal will be affected by the number of repeat units in a single isoform. Once again, if a standardized reference having known isoform composition and known mass was included in the assay, this might overcome this source of bias. Furthermore, some cross reactivity may occur between kringle 4 and plasminogen (a serum protein). Other methods for measuring Lp(a) in human plasma include nephelometry, electro-immunodiffusion, lipoprotein agarose electrophoresis (used in conjunction with ultracentrifugation) and rocket electrophoresis.

The measurement of mass of apo(a) could be informative if a suitable standardized reference of Lp(a) of single or pooled known isoform(s) were available.

One of the existing problems concerning the production of a standardized reference preparation of Lp(a) is the complexity and variability of existing methods of production of Lp(a). Existing methods of producing Lp(a) free of contaminating lipoproteins and laborious, time consuming and inefficient and are therefore not suitable as routine methods for producing large amounts of Lp(a) (Gaubatz et. al. *Methods in Enzymology*, 129:167–186 (1986).

There is a need at this time for a standardized reference method and material for routine use in measuring Lp(a) in clinical samples. A simple, reproducible method for preparing large amounts of Lp(a) that are free of particles belonging to other lipoprotein classes is required to facilitate the production of a standardized reference preparation.

SUMMARY OF THE INVENTION

The invention includes, in one aspect, a method for preparing substantially any and all lipoprotein(a)(Lp(a)) from a volume of a biological fluid sample, that is substantially free of lipoproteins of another class. The method involves subjecting the sample to ultracentrifugation, collecting at least one fraction containing Lp(a) after centrifugation; subjecting the fraction(s) to a reaction with a stabilized ligand for selectively binding interfering substances, the Lp(a) remaining unbound; and obtaining the non-reacted Lp(a) in a liquid phase in a form being substantially free of interfering lipoproteins.

In another embodiment of the invention, a method of preparing Lp(a) from a biological fluid sample that is substantially free of lipoproteins of another class and substantially free of plasma proteins, is provided that includes the steps of preparing Lp(a) by ultracentrifugation followed by ligand absorption, and a filtration step, further reacting the Lp(a) in the filtrate with an immobilized ligand wherein the ligand binds a component of the Lp(a) selected from the group consisting of apo(a) protein, apo $B_{100}$, and Lp(a) associated oligosaccharide; eluting the bound Lp(a) from the ligand; and subsequently obtaining Lp(a) that is substantially free of biological molecules other than Lp(a).

In a further embodiment of the invention, a method for measuring an amount of one or more isoforms of Lp(a) in a biological fluid in the presence of interfering lipoproteins, is provided having the following steps: ultracentrifuging the biological fluid in the presence of a salt having a density suitable for separating high density lipoproteins (HDL) from low density lipoproteins (LDL); adding the HDL fraction obtained after ultracentrifugation to a reaction chamber of a disposable device, for reacting with a stabilized ligand contained therein, the ligand being capable of selectively binding interfering substances; causing substantially all non-reactant material, including the Lp(a) to be removed from the reaction device into a collection chamber through a filter, the ligand-bound interfering substance remaining in the reaction device; and conducting a clinical assay for Lp(a) on the non-reactant filtrate including Lp(a) in the presence of a standardized reference.

In another embodiment of the invention, a method for analyzing lp(a) in a clinical sample is provided having the steps of (a) obtaining a standardized preparation of Lp(a), prepared by first, subjecting the sample to ultracentrifugation; second, after centrifugation, collecting at least one fraction containing Lp(a); third, subjecting at least one fraction to a reaction with an immobilized ligand for selectively binding the interfering cholesterol-containing lipoprotein in another class, the Lp(a) remaining unbound; and fourth, collecting the unbound Lp(a) in a liquid phase, the preparation being suitable for use in the analysis of any of protein concentration, protein isoform determination or cholesterol assays; and having a known mass and cholesterol content for acting as a reference for Lp(a) in the sample; (b) preparing the clinical sample so as to remove interfering substances according to a method having the following steps: first, preparing Lp(a) according to the steps outlined in (a); second, reacting the Lp(a) with an immobilized ligand which is an immune reagent having specificity for at least one of the group consisting of apo (a), Lp(a), apo B100, kringle 4 of Lp(a), kringle 5 of Lp(a) and the protease domain of Lp(a); third, eluting the bound Lp(a) from the ligand; and fourth, collecting the unbound Lp(a) that is substantially free of biological molecules other than Lp(a); and (c) performing an analysis on the clinical sample and the standardized reference to obtain a quantitative value for Lp(a) in the clinical sample.

In a further embodiment of the invention, a standardized reference is described for measuring Lp(a) in a clinical sample that includes a plasma preparation containing Lp(a) prepared according to the two phase preparation method involving ultracentrifugation, ligand adsorption of interfering substances and filtration, wherein the preparation is substantially free of interfering substances and has a known Lp(a) mass and Lp(a) cholesterol content.

DETAILED DESCRIPTION OF SPECIFIC EMBODIMENTS

Figure 1:
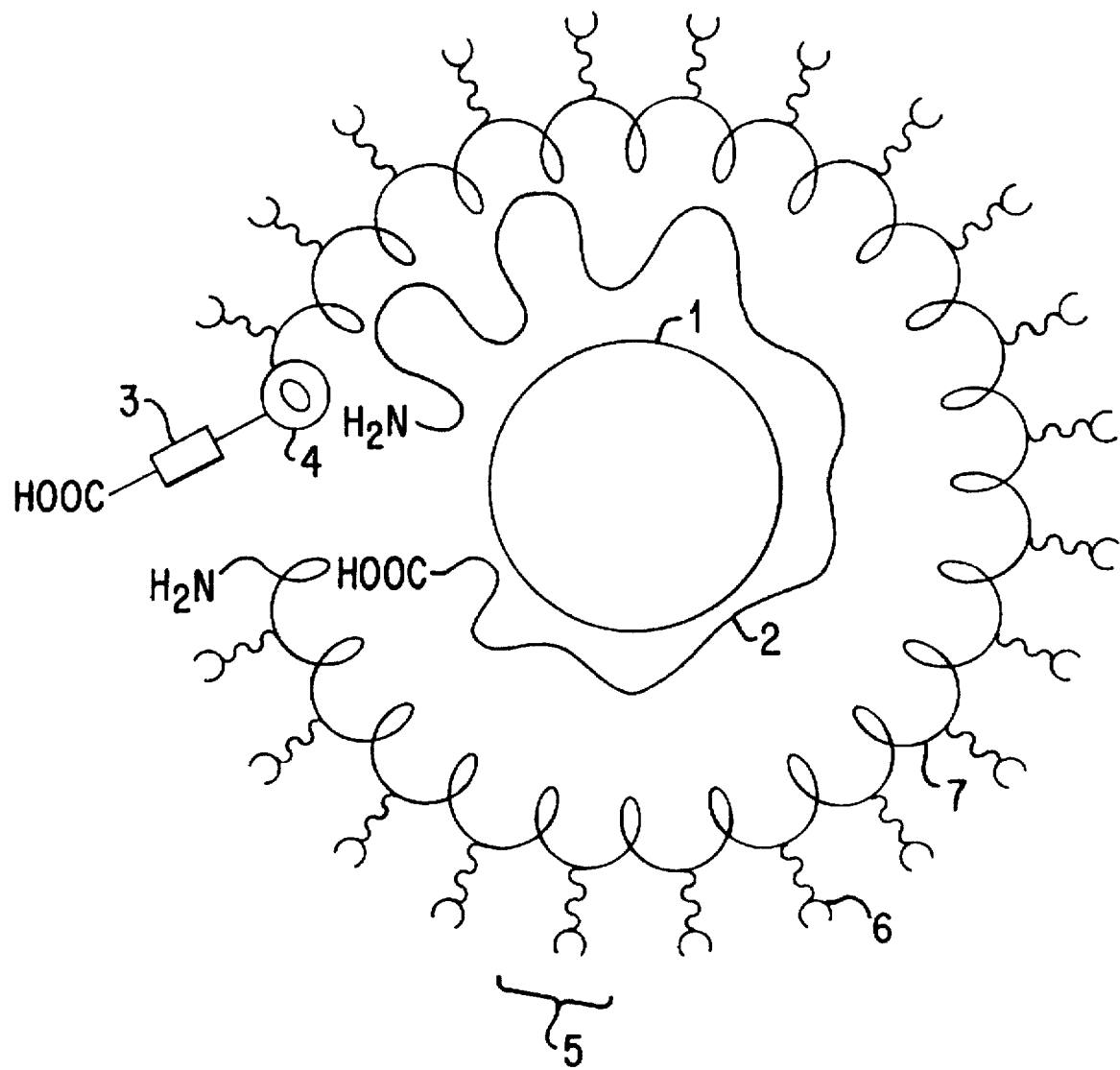
FIG. 1 is a schematic model of Lp(a) showing the central LDL particle with 1 molecule of apo(a) attached at the surface. The multiple repeat units of kringle 4 with associated oligosaccharide are shown, with the kringle 5 domain and protease at the C-terminal end of the molecule.
Figure 2:
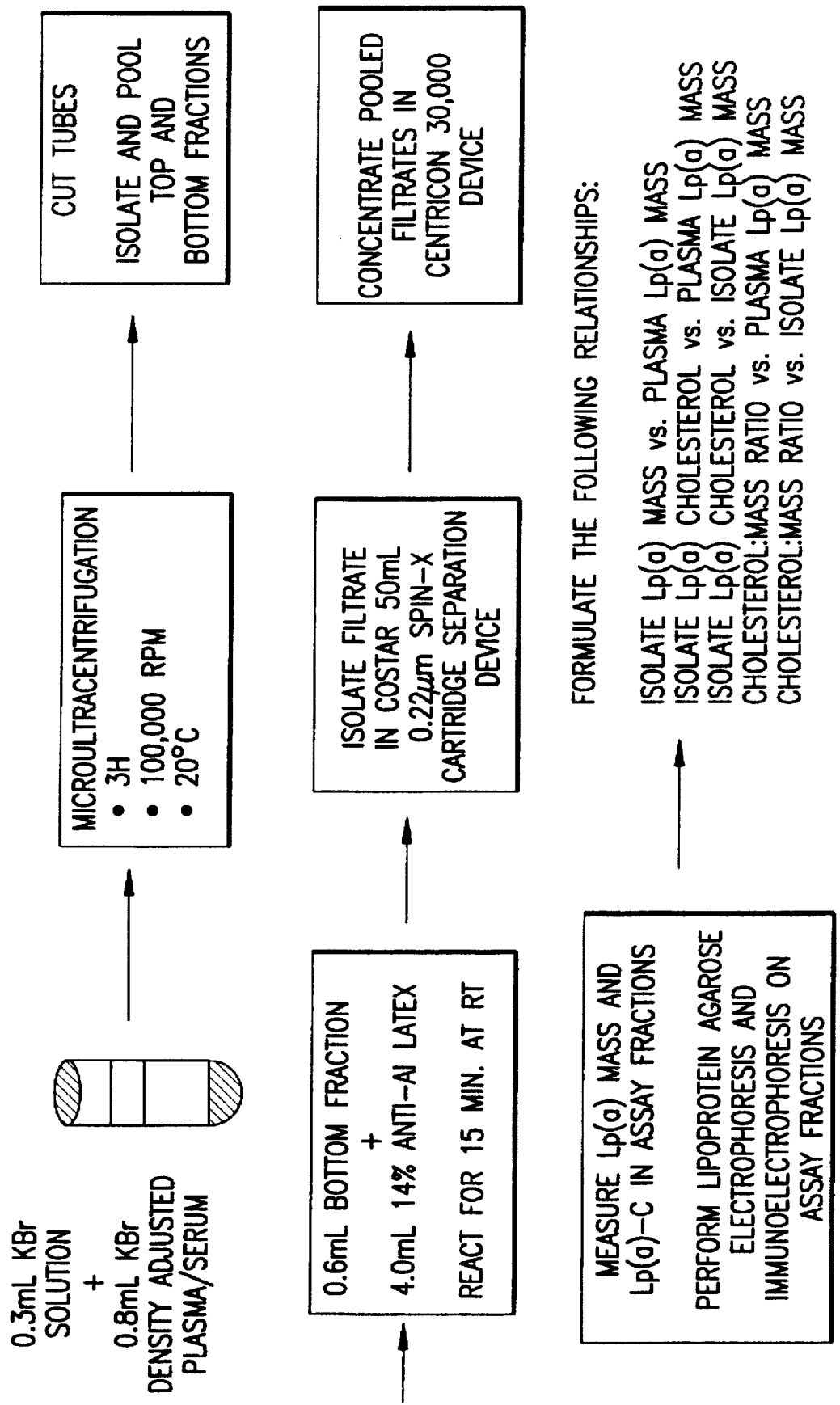
FIG. 2 is a schematic diagram showing the isolation of Lp(a) from individual clinical samples.
Figure 3:
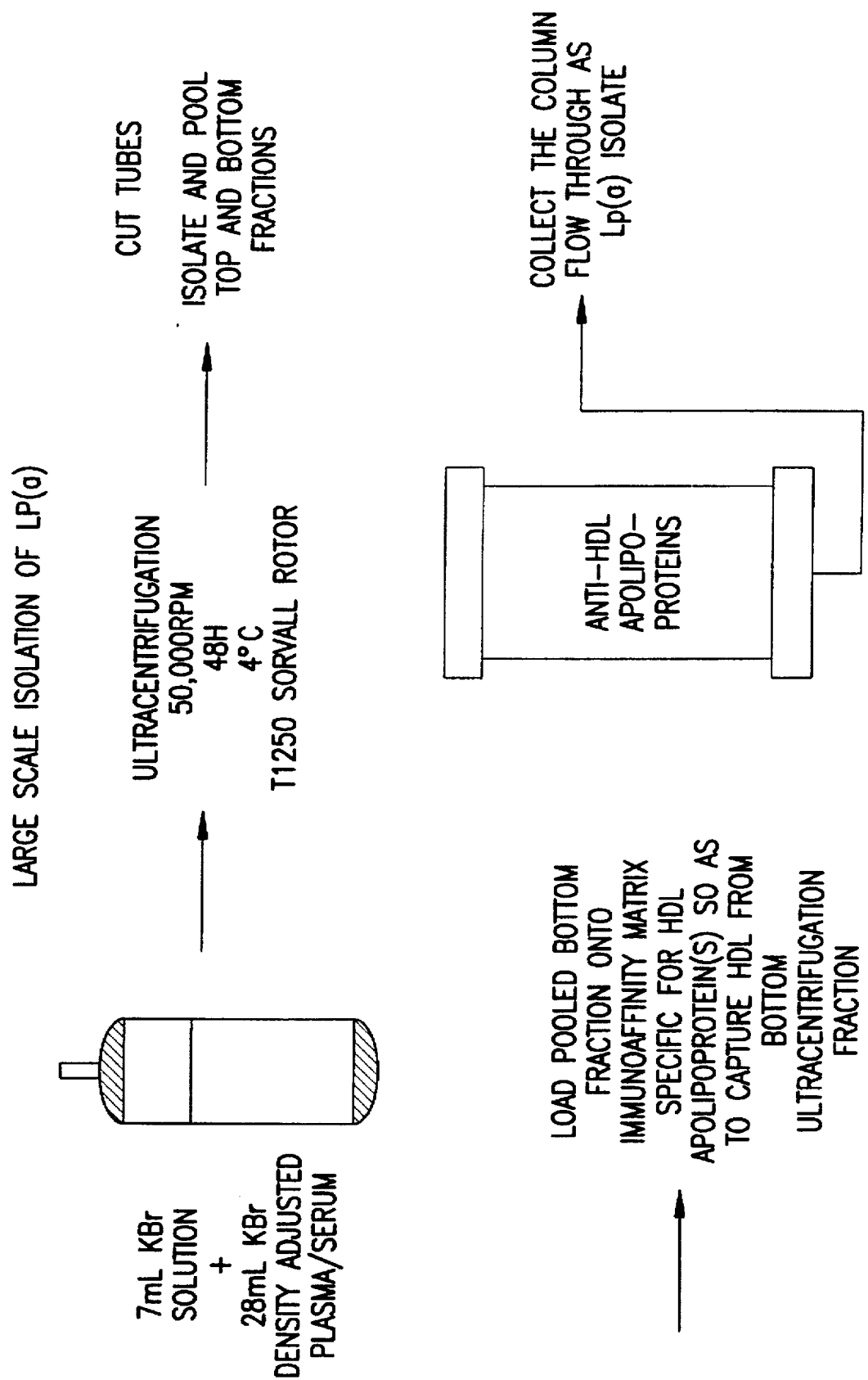
FIG. 3 is a schematic diagram showing the large scale isolation of Lp(a).

Separation of high density lipoproteins including Lp(a) from low density lipoproteins by ultracentrifugation.

The major classes of lipoproteins, based on their buoyant densities, are VLDL ($\leq 1.006$ kg/L), LDL (1.006–1.063 kg/L) and HDL (1.063–1.21 kg/L). The buoyant density of the Lp(a) particles ranges from 1.050 kg/L to 1.110 kg/L, thus overlapping the density ranges of LDL and HDL particles. The method described here utilizes gradient ultracentrifugation at a density of 1.05 kg/L. At that density chylomicrons, VLDL and LDL collect at the top of the solution in the ultracentrifugation tube and Lp(a) and HDL collect at the bottom of the tube.

Removal of Interfering Substances (HDL) by ligand binding.

Once the supernatant in the top portion has been removed, the high density components in the bottom fraction (containing HDL, Lp(a) and plasma proteins in solution and partially sedimented as a pellet) are resuspended. The principal interfering substance in the resuspended pellet is high density lipoprotein (HDL). It is desirable to remove HDL because the cholesterol contained in HDL interferes with the cholesterol determination of Lp(a).

A preferred method of removing the interfering substance according to the invention, is to adsorb the substance to a ligand, for example an antibody that selectively binds the substance and not the analyte. A method and device for achieving this separation has been described in detail and claimed in the parent application 08/393,337, and in U.S. Pat. No. 5,403,745 incorporated here by reference. In a preferred embodiment, the ligand for reacting with interfering substances (HDL) is a preparation of antibodies that may be immobilized on a number of substrates. Ligands other than antibodies may also be employed, if the ligand selectively binds the interfering substances and not Lp(a).

Examples of antigen binding molecules include polyclonal antibodies, monoclonal antibodies, recombinant antibodies and antibody fragments as well as mixtures of any of the above. In one embodiment of the invention, a reaction device is used to rapidly and inexpensively implement the immunoreaction-separation. The antibodies used in the immunoreaction may be freeze dried or used as preparation on a suitable carrier. A wide range of suitable carriers and separation techniques for this purpose are available. Thus the antibodies may be bound to the surface of an insoluble carrier whose mass, density, surface area or charge will facilitate separation of immuno-reactants from non-reactants. Examples of insoluble carriers are microporous beads, latex particles, magnetic particles, controlled pore glass, gel matrices from cross linked dextran, cross linked polysaccharides, or cross linked acrylamide, microporous filters or membranes. Other suitable insoluble carriers include a coiled strip or the interior wall of the reaction device itself. Antibodies may also be bound to soluble large MW polymers to effect a more readily precipitable immune complex with the analyte. Examples of suitable polymer carriers are polysaccharides, proteins or polynucleotides. This approach can also enhance the kinetics of the immunoseparation. The immunoreacting antibodies may be either polyclonal or monoclonal or mixtures of either or both, provided they possess sufficient specificity, lack of cross-reactivity, ability to quantitatively absorb to a broad range of substrate concentrations, and separability of the immuno-reacted complexes.

In order to remove HDL from the high density lipoprotein fraction, antibodies have a specificity to apolipoprotein A antigens including Apo AI, Apo AII and Apo AIV; apolipoprotein C antigens including Apo CI, ApoCII and ApoCIII and Apolipoprotein E antigens including ApoE1, ApoE2, ApoE3 and ApoE4 can be used.

In embodiments of the invention, the stabilized antibody which may also be immobilized, may be added to the resuspended pellet of high density lipoprotein after the sample is placed in the reaction chamber. In another embodiment of the invention, the ligand preparation is already present in the reaction chamber before the sample is added.

After adsorption of the interfering substances to the ligand, the non-reacted material may be transferred to a collection chamber either directly or following a subsequent filtration step. The non-reacting material including Lp(a) is then physically separated from the interfering substances bound to the ligand, by means of a filtration or chromatography step.

The advantage of the methodology outlined above with respect to Lp(a) is clear. Because the methodology seeks to exclude interfering substances instead of binding analyte, the problems associated with bias that arise out of the numerous isoforms of Lp(a) are avoided. All isoforms in the sample of biological fluid will be represented in the naturally occurring amounts using the embodiments of our invention.

Having obtained the Lp(a) in the filtrate, a concentration step can be performed to provide a concentration of Lp(a) suited for use as a reference standard.

The two-step method described above may be used to prepare large volumes of Lp(a) derived from a patient or group of patients. The two step method is also suited for preparing small volume samples for use in assays to quantify the amount of Lp(a) present in each of a population of subjects.

In certain circumstances such as for performing biochemical analysis, it is desirable to separate Lp(a) from plasma proteins. In this situation, we have passed the Lp(a) containing plasma proteins over a substrate containing ligand for binding Lp(a). Examples of such ligands include polyclonal, monoclonal or recombinant antibodies to apo(a), Lp(a), apoB100, kringle 4, kringle 5, or the protease domain. Lectins (including wheat germ agglutinin), lysine and fibrin analogues (such as desafib-X (Leerink, *Fibrinolysis* 8:214–220 (1994)) can also be used. Polyanions (such as dextran sulfate or heparin manganese) can be used to bind Lp(a), but, because they interact with apoB$_{100}$, other lipoproteins (including VLDL and LDL) will also be bound and precipitated.

The methods for measuring cholesterol content of Lp(a) and also for determining the mass of a sample have been established in the art. Methods for performing these quantitative analyses are provided below.

1. Assays for Determining Lp(a) Mass.

Commercial assays are used here to determine the mass of the samples of Lp(a) prepared according to our invention. For example The Macra Lp(a) assay is an ELISA-based assay and is available from Strategic Diagnostics, Newark, Del. The capture antibody is a monoclonal anti-Lp(a) and the detection antibody is a polyclonal anti-Lp(a) conjugated with horseradish peroxidase. The PerImmune (Organon Teknika/Biotechnology Research Institute) assay is also an ELISA based assay. The capture antibody is a monoclonal anti-apo(a) antibody and the detection antibody is a polyclonal anti-apoB100 conjugated with horseradish peroxidase. The Incstar Lp(a) assay is an immunoprecipitin or immunoturbidimetric assay. The antibody used is a polyclonal anti-Lp(a). Any of these methods are suited for determining mass of Lp(a).

2. Assay for determining Cholesterol Content.

Total cholesterol is determined enzymatically using cholesterol esterase, cholesterol oxidase and other enzymes and reagents which translate the oxidation of cholesterol into a detectable color change. For example, cholesterol oxidase generates $H_2O_2$ in the presence of free cholesterol, a peroxidase enzyme and a peroxidase substrate dye which undergoes a profound color change when it is oxidized by $H_2O_2$ in the presence of the peroxidase enzyme. Such peroxidase/dye systems for quantitating cholesterol are well known in the art.

3. Identification of the Apo(a) isoform.

Lp(a) isoforms prepared according to the embodiments of our invention can be determined using methods described previously for example, by Craig, *Appl. Theor. Electrophoresis*, 2:135–140 (1991), and Gaubatz, *J. Lipid Res.*, 31:603–613 (1990). Proteins in human serum are denatured by boiling in the presence of a sodium dodecyl sulfate (SDS) and a reducing agent. Under these conditions, the apo(a) dissociates from the apoB of the Lp(a). The material is then electrophoresed in agarose or acrylamide gradients, such that the apo(a) can be efficiently separated based on its size, which is directly dependent on the number of kringle 4 repeats present in the structure. The separated protein is then electrophoretically transferred to a solid support such as nitrocellulose or Immobilon known in the art as a western blot. The western blot is then reacted with an apo(a) antibody (the primary antibody immunoreaction). An appropriate enzyme-labeled secondary antibody (that specifically reacts with the primary antibody) is used for detection of the different apo(a) isoforms.

4. Determination of Lipoprotein Purity:

(a) Lipoprotein Agarose Electrophoresis (LAE).

Figure 5:
FIG. 5 shows the results of the immunoelectrophoresis analysis of fractions with the sample tracks showing, from left to right, plasma reacted with anti-apoAI; two ultracentrifugation fractions (UCF Top and UCF Bottom) reacted with both anti-Lp(a) and anti-apoAI, and 5 isolated Lp(a) fractions (Lp(a) samples 1 through 5) reacted with both anti-Lp(a) and anti-apoAI.

Lipoproteins can be separated based on their charge in 1% agarose in a pH 8.6 barbital buffer (Ciba Corning Diagnostics Corp., Universal Gel System and Universal PHAB Buffer Set). The lipoproteins which can be resolved are VLDL, LDL, Lp(a) and HDL (FIG. 5). LDL is considered a beta-lipoprotein, VLDL and Lp(a) are pre-beta lipoproteins and HDL is an alpha lipoprotein. Unfractionated serum/plasma and/or the isolated fractions are applied to the sample wells and electrophoresed in the PHAB buffer for 30 minutes at room temperature. Separated lipoproteins are visualized using Fat Red or Amido Black lipoprotein stain.

(b) Description of Immunoelectrophoresis (IEP).

The first phase of IEP involves LAE, where the lipoproteins contained within the unfractionated serum/plasma and/or the isolated fractions being analyzed are separated based on their charge in a 1% agarose gel (as described in 4a, above). The second phase of the analysis involves applying antibodies, typically monospecific, affinity-purified antibodies, to the sample troughs of the gel. Antibodies are applied to separate troughs. The gels are incubated overnight at room temperature in a humidified chamber. This allows the lipoproteins and the antibodies to diffuse through the agarose gel toward each other, react specifically and precipitate in the gel in the form of an immunoprecipitation arc. The gel is washed for a minimum of 6 hours in phosphate buffered saline with gentle agitation to remove all soluble, non-precipitated protein. Immunoprecipitates are visualized by staining with Coomassie Blue R Staining and documented by photography, scanning or other means known in the art.

c) Analysis of the Purity of Isolated Lp(a).

Figure 4:
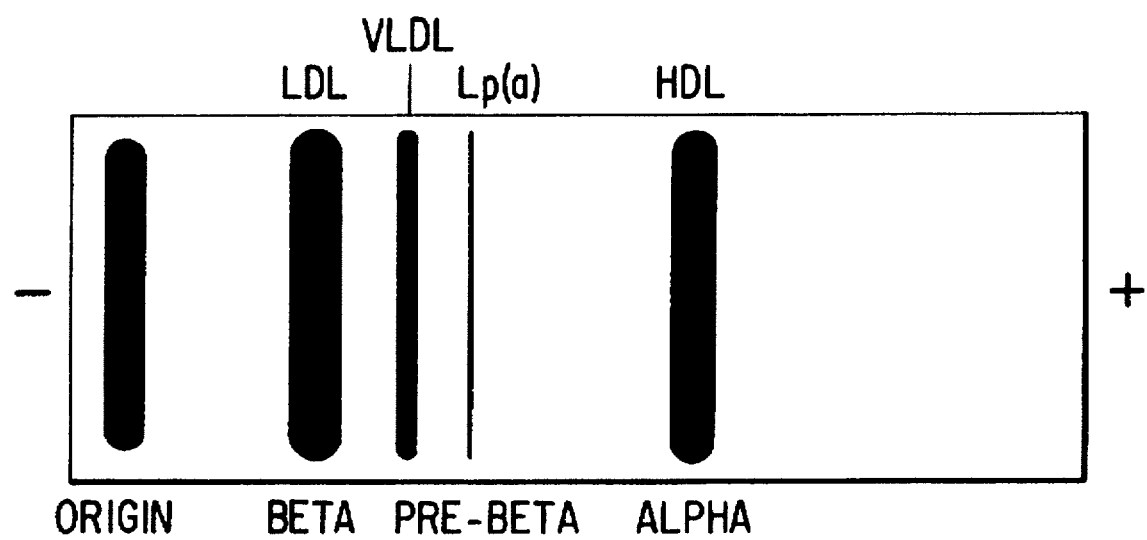
FIG. 4 is a schematic diagram of lipoprotein separation upon lipoprotein agarose electrophoresis.

IEP is used to characterize the lipoprotein content of the isolated Lp(a). In one embodiment, affinity-purified anti-apoAI is used to detect the presence of HDL in the samples. Similarly, Lp(a) isolated by the clinical method are reacted with anti-Lp(a) (see FIG. 4). The results indicate that the Lp(a) isolates are positive for the presence of Lp(a) and negative for the presence of HDL. In one experiment Lp(a) isolates were concentrated up to eight fold using Centricon 30 devices. The concentrated material was subjected to IEP and probed with affinity-purified anti-apoAI. No HDL was detected in four of the five samples tested. HDL at a concentration of between 1 and 3 mg/dL HDL-C was detected in one of the five samples analyzed. This sample probably had a high HDL-C serum value. Lp(a) isolates were also analyzed by LAE followed by Fat Red staining. The isolates always presented as single lipoprotein bands, which reacted with anti-Lp(a), indicating the absence of other pre-beta, beta and alpha lipoproteins.

Lp(a) isolates have also been electrophoresed in 4–20% acrylamide gradient gels, under SDS and reducing conditions, and blotted with affinity-purified anti-apoAI. The blots indicate that Lp(a) isolates do not contain apoA1, showing that the samples are devoid of HDL contamination.

5. Methods of Storage of Lp(a) Standardized Preparations.

Methods for preparing lipoproteins in a stable formulation so as to preserve structure and composition of the particles during long shelf life storage include lyophilization or liquid stabilized formulation of Lp(a) purified by the methods of the invention and present in plasma or a predefined buffer. Alternatively Lp(a) may be formulated in a reconstituted delipidated serum for lyophilization or storage in a liquid stabilized form. An embodiment of a liquid storage medium is provided in parent applications 08/198,919 and 08/198,430 here incorporated by reference. For example, Lp(a) may be stored in a liquid stabilized formulation including defibrinated, sodium free blood plasma, a glass forming sugar, a serum albumin and/or gelatin and a potassium salt.

EXAMPLES

Example 1

Isolation of Lp(a) from Clinical Samples.

A volume of 2.0 mL of human plasma or serum, per sample being analyzed, was adjusted to a density of 1.05 kg/L by adding 0.147 grams of oven dried potassium bromide to the sample. The sample was gently mixed until the salt was dissolved and 0.8 mL of the density-adjusted sample was added to duplicate labeled ultracentrifuge tubes (Beckman polycarbonate 11×34 mm, catalog number 323778). The sample in each tube was overlaid with 0.3 mL of a potassium bromide (KBr) solution having a density of 1.05 kg/L. The samples were centrifuged in a fixed angle rotor in a Beckman Optima TLX Tabletop Microultracentrifuge for 3 hours at 300,000 revolutions per minute (RPM) at 20° C. The tube cutting stage of the Beckman tube slicer was set so that tubes were cut at a height of approximately 1.3 cm. The tube was cut with a blade that formed a partition between a top fraction and a bottom fraction. The top fraction was carefully removed (and saved for later analysis) using a Pasteur pipet. The blade retracted and the bottom of the tube was removed from the apparatus. With a separate clean pipet, the bottom fraction was carefully resuspended, making sure that the gelatinous pellet which forms at the bottom of the tube was completely solubilized. The top fraction was saved separate from the bottom fraction from each tube and the saved top fractions from duplicate samples were combined. Likewise the bottom fractions saved from duplicate samples were combined. The volume of each bottom fraction was measured and recorded (for converting to volume from a measured weight, a density value of 1.05 g/mL was used). The final volume of the bottom fraction was brought to 1.6 mL with phosphate-buffered saline (PBS). The volume of PBS required to bring the bottom fraction to a volume of 1.6 mL was recorded.

Where the bottom fractions was not brought up to a volume of 1.6 mL with PBS, or if the volume of bottom fraction collected was greater than 1.6 mL, a bottom fraction correction factor was calculated by dividing 1.6 mL by the bottom fraction volume. Bottom fraction Lp(a) mass and cholesterol values were divided by this correction factor. Where the top fractions were saved and pooled, a correction factor for top fraction measurements was calculated by dividing 1.6 mL by the top fraction volume and the top fraction was divided by this correction factor.

From the bottom fraction, 0.6 ml was combined with 4 ml of anti-A1 latex (14–15% solids:supplied by Genzyme) in a 50 mL Costar 0.2 µm Spin-X cartridge separation device (Baxter 8306DS). The mixture was incubated for 15 minutes at room temperature with intermittent, gentle mixing. The filtrate and retentate were separated by centrifuging in a tabletop centrifuge (Beckman GS-6R centrifuge, GA-10 rotor, 5500 RPM, 3600×g, 30 minutes, or equivalent). The top reaction chamber containing the sedimented latex was discarded. The total volume of filtrate recovered from each sample was measured and recorded. Of each filtrate, 2.5 mL (representing a fraction of the total) was concentrated by centrifugation (in a Beckman GS-6R centrifuge, GA 24 rotor at 3740 RPM (approximately 2000 g for 40 mins) to approximately 330 µL (a 7.6 fold concentration) using Centricon 30 devices (Amicon 4209) device. The percentage of the filtrate for concentration was recorded for later mass balance calculations (total volume of filtrate/2.5 mL). The final volume of the concentrated material was measured and recorded. A correction factor for all subsequent analysis was calculated by dividing 7.6 by the actual, calculated concentration factor. All assay fractions and final samples were analyzed for Lp(a) mass, using nephelometric, ELISA or electrophoretic assays and for Lp(a) cholesterol, using standard enzymatic cholesterol assays. Assay fractions and final samples were also analyzed using lipoprotein agarose gel electrophoresis and immunoelectrophoresis to investigate the lipoprotein content of the sample.

Example 2

Large Scale Isolation of Lp(a).

The ultracentrifugation methodology described in Example 1 was scaled up 35 fold ultracentrifuge. Human plasma (or serum) was adjusted to a density of 1.05 kg/L by adding 24.7 grams of oven dried potassium bromide to the sample. The sample was gently stirred until the salt was dissolved. Twenty eight ml of the density adjusted sample was added to each centrifuge tube (DuPont Sorvall 35 mL polyallomer tubes, Catalog number 03935). Seven (7) ml of a density 1.05 Kg/l KBr solution was carefully overlaid each sample. The tubes containing the samples were centrifuged in a fixed angle rotor in a Sorvall OTD55B ultracentrifuge for 48 hours at 50,000 RPM at 20° C. The tubes were sliced at a height of approximately 5 cm and top and bottom fractions were saved separately. After the volume of each combined fraction was measured and recorded, the combined bottom fraction was filtered through a 0.2 micron filter and passed through an immunoaffinity column composed of an insoluble immunoaffinity matrix that was specific for HDL apolipoproteins. (for example: affinity-purified anti-apoAI chemically immobilized to a solid support such as Toyopearl Tresyl A650M supplied by TosoHaas) and equilibrated with PBS, 0.5M sodium chloride. The immunoaffinity column was equilibrated prior to loading and washed with PBS, 0.5M sodium chloride until a baseline absorbance was reached. The load and wash effluent peak was collected containing HDL stripped, pure Lp(a). The bound HDL was eluted from the immunoaffinity column using 0.1M Glycine pH 2.2±0.2. The column was reequilibrated with PBS, 0.5M sodium chloride. The immunoaffinity column can be used repeatedly for the separation of HDL and Lp(a) in the bottom ultracentrifugation fraction. As described in Example 1, all purification fractions and final samples can be analyzed for Lp(a) mass, using nephelometric, ELISA or electrophoretic assays, and for Lp(a) cholesterol, using standard enzymatic cholesterol assays. Purification fractions and final samples may also be analyzed using lipoprotein agarose gel electrophoresis and immunoelectrophoresis to investigate the lipoprotein content of the sample.

Example 3

Preparation of a Standardized Reference for Lp(a) Assays

A preparation of Lp(a) was prepared according to Example 2. HDL stripped pure Lp(a) was obtained and concentrated by standard methods such as ultracentrifugation so as to obtain a concentration at which the Lp(a) can be stored conveniently in a formulation that preserves the structure and composition of the Lp(a) over the long term. Although numerous methods known in the art may be used for concentrating the Lp(a) preparation, a molecular weight cutoff filtration method was used here. This method utilizes a filter that is porous to molecules having a molecular weight of less then 30,000 MW. To material concentrated in this way, a storage buffer may be added to prolong shelf life. An example of a storage buffer includes a buffer solution, for example 50–150 mM Hepes, a stabilizing protein (for example 5% bovine serum albumin) and a sugar. An alternate storage buffer has been described in application 08/198, 430, here incorporated by reference.

This preparation may then be diluted as required by the assay for which the standardized reference is to be used. For example, an ELISA assay may require Lp(a) at a concentration of 150 mg/L to 600 mg/L in 1 ML aliquots. The current threshold value for Lp(a) has been determined to be about 300 mg/L below which, there is no medical concern, and above which there is medical concern. The standardized reference may be prepared in aliquot sizes in a prediluted form as required for ease of use for performing Lp(a) analysis of clinical samples by determining either mass or cholesterol content. Alternatively, the standardized reference may be prepared in concentrated form for dilution at the site where the assay is performed.

The isoform characteristics of the Lp(a) in the standard reference sample may be determined according to the method provided above. With an appreciation of the isoform type, the quantification of Lp(a) mass and cholesterol content in the standard sample can be determined to a high degree of accuracy using conventional assay techniques described above.

The standardized reference produced according to the method of the invention provides for the first time, an Lp(a) preparation suitable for determining both mass and cholesterol measurements of clinical samples.

Although the invention has been described with respect to particular embodiments and methods, those skilled in the art will know or be able to ascertain using no more than routine experimentation, many equivalents to the specific embodiments of the invention described herein. These and all other equivalents are intended to be encompassed by the following claims.

Example 4

Characterization of isolated Lp(a)

Fractions from the Lp(a) isolation procedure described in example 1 and example 2, were electrophoresed and reacted with two antibodies, anti-Lp(a) and affinity purified anti-apoAI (antiAI). The anti-Lp(a) was used to positively indicate the presence of Lp(a) in the fractions, while the affinity purified anti-ApoA1 was used to detect the presence of contaminating HDL in the fractions. The presence of an immunoprecipitation arc indicated a positive reaction (see FIG. 5). In this experiment, five individual plasma samples were processed for the isolation of Lp(a). The samples which were analyzed were whole plasma (the material from which one of the Lp(a) fractions were isolated) a representative ultracentrifugation (UCF)top fraction, a representative ultracentrifugation bottom fraction and the five isolated Lp(a) fractions. The table below summarizes the results with a plus sign (+) indicating a positive reaction and a negative sign (−) indicating a negative reaction. NA indicates that the fraction was not probed with anti-Lp(a). Differences in the intensities of the immunoprecipitation arcs indicate differences in the concentration of the lipoprotein being analyzed.

TABLE 1

| Sample | Anti-Lp (a) Immunoreactivity | Anti-apoAI Immunoreactivity |
|---|---|---|
| Whole Plasma | NA | + |
| UCF Top Fraction | − | − |
| UCF Bottom Fraction | + | + |
| Lp(a) 1 | + | − |
| Lp(a) 2 | + | − |
| Lp(a) 3 | + | − |
| Lp(a) 4 | + | − |
| Lp(a) 5 | NA | − |

As measured by the PerImmune Macra Lp(a) ELISA Kit, the twelve samples analyzed had Lp(a) mass levels of between 7.97 and 113.49 mg/dL. The recovery of Lp(a) mass by the method described within ranged from 74.5% to 110.2% with an average of 93.3%. Lp(a) cholesterol values ranged from 3.54 to 15.99 mg/dL. Cholesterol to mass ratios, where the plasma Lp(a) mass was utilized ranged from 14.8% to 59.6%. The average ratio was 27.1%, which strongly agrees with the average ratio determined by Seman, et al., *Clin. Chem.* 40:400–403 (1994). Cholesterol to mass ratios, where the isolate Lp(a) mass was utilized, ranged from 14.1% to 44.4%. The average ratio was 25.4%, which again strongly agrees with the average ratio determined by Seman, et al. These results show that the isolated Lp(a) fractions were free of contamination by other lipoproteins.

Figure 6:
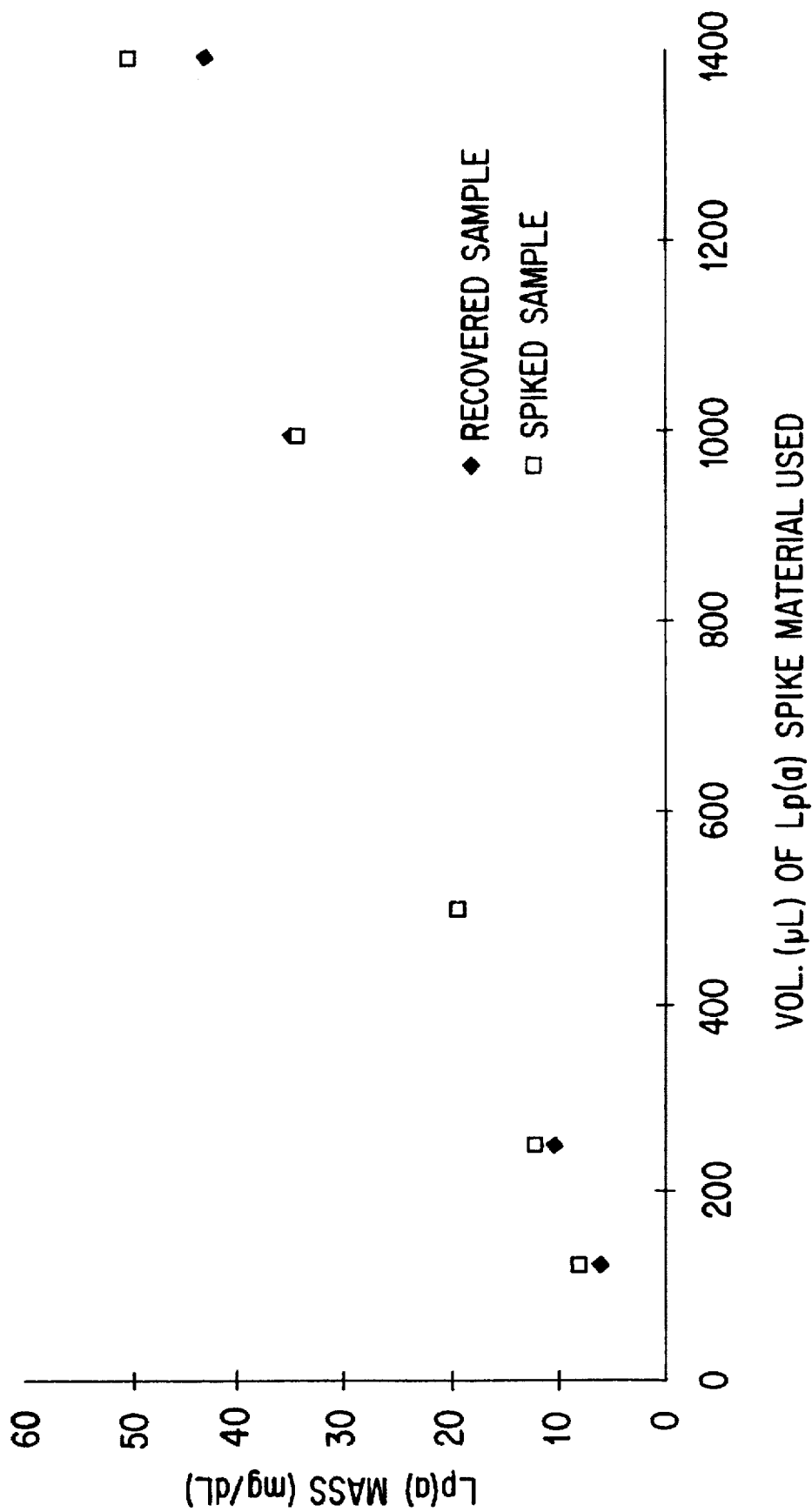
FIG. 6 is a graph showing the results of a purified Lp(a) spike and recovery experiment.

In a further experiment to characterize the Lp(a) isolation method, a spike and recovery experiment was undertaken. Using the method described in Example 2 and a plasma sample with a high Lp(a) concentration, Lp(a) suitable for use as spiking material was isolated. Increasing volumes of the Lp(a) spike material were combined with a different plasma sample having a low baseline Lp(a) concentration. Five Lp(a) spiked samples were prepared in this manner. The volumes of Lp(a) spike used are indicated in FIG. 6. The five spiked samples were then brought through the Lp(a) isolation method described in Example 1. Lp(a) mass was measured in the initial spiked fraction (spiked sample) and the resulting isolated Lp(a) fraction (recovered sample). The

TABLE 2

| | | | Lp(a) % | | Cholesterol to Mass Ratio | |
|---|---|---|---|---|---|---|
| SAMPLE | Plasma Lp(a) Mass (mg/dL) | Isolate Lp(a) Mass (mg/dL) | Recovery Isolate/Plasma | Isolate Lp(a)-C (mg/dL) | Isolate Lp(a)(%) | Plasma Lp(a)(%) |
| 1 | 25.21 | 22.84 | 90.6 | 7.57 | 33.1 | 30.0 |
| 2 | 28.12 | 30.99 | 110.2 | 9.79 | 31.6 | 34.8 |
| 3 | 48.44 | 48.14 | 99.4 | 10.32 | 21.4 | 21.3 |
| 4 | 56.4 | 56.38 | 100.0 | 8.35 | 14.8 | 14.8 |
| 5 | 43.74 | 45.61 | 104.3 | 11.91 | 26.1 | 27.2 |
| 6 | 56.38 | 44.68 | 79.3 | 8.97 | 20.1 | 15.9 |
| 7 | 113.49 | 103.07 | 90.3 | 15.99 | 15.5 | 14.1 |
| 8 | 7.97 | 5.94 | 74.5 | 3.54 | 59.6 | 44.4 |
| 9 | 12.19 | 10.46 | 85.8 | 4.03 | 38.5 | 38.5 |
| 10 | 19.36 | 19.09 | 98.6 | 5.05 | 26.5 | 26.5 |
| 11 | 34.34 | 34.99 | 101.9 | 6.74 | 19.3 | 19.3 |
| 12 | 50.23 | 42.88 | 85.4 | 7.92 | 18.5 | 18.5 |
| RANGE: | 7.97–113.49 | 5.94–103.07 | 74.5–110.2 | 3.54–15.99 | 14.8–59.6 | 14.1–44.4 |
| AVERAGE: | | | 93.3 | | 27.1 | 25.4 |

Al lp(a) mass values were determined in duplicate using the Perimmune Macra Lp(a) ELISA Kit.

Table 2 indicates the results obtained from the processing of 12 patient samples for the isolation of Lp(a) as described in Example 1. For each sample the following analytes were measured: whole plasma Lp(a) mass, the Lp(a) mass of the isolated fraction and the cholesterol content (Lp(a)-c) of the isolated fraction. From these determinations the following determinations were made: percent recovery of Lp(a) mass, that is the isolate Lp(a) mass divided by the whole plasma Lp(a) mass multiplied by 100, the cholesterol to mass ratio where the whole plasma Lp(a) mass is used in the determination and the cholesterol to mass ratio where the isolate Lp(a) mass is used in the determination. The cholesterol to mass ratio is calculated by dividing the Lp(a) cholesterol by the Lp(a) mass and multiplying by 100. The cholesterol to mass ratio determination was used as an indicator of the lipoprotein purity of the isolated sample. Contaminating lipoproteins in the Lp(a) isolate will carry cholesterol and ultimately result in an inflation of the cholesterol to mass ratios obtained.

results are presented in FIG. 6. The data show that using the methods of the invention, Lp(a) was quantitatively recovered from the spiked samples.

We claim:

1. A method for preparing substantially any and all lipoprotein (a) (Lp(a)), from a volume of a biological fluid sample, so as to remove interfering cholesterol-containing lipoprotein, of another class, the method comprising:

(i) subjecting the sample to ultracentrifugation;

(ii) after centrifugation, collecting at least one fraction containing Lp(a);

(iii) subjecting the at least one fraction to a reaction with an immobilized ligand for selectively binding the interfering cholesterol-containing lipoprotein of another class, the Lp(a) remaining unbound; and (iv) collecting the unbound Lp(a) in a liquid phase, the preparation being suitable for use in the analysis of any of protein concentration, protein isoform determination or cholesterol assays.

2. A method according to claim 1, wherein step (i) is preceded by the step of adding a solution of a salt to the sample, the salt having a density capable of separating high density lipoproteins from low density lipoprotein including very low density lipoproteins during centrifugation.

3. A method according to claim 2, wherein step (i) further comprises the step of ultracentrifuging the sample so as to form a bottom fraction containing high density components, these component including substantially all the Lp(a) present in the biological fluid.

4. A method according to claim 3, wherein step (ii) further comprises the steps of isolating and resuspending the bottom fraction.

5. A method according to claim 4, wherein step (ii) further comprises the step of adding the resuspended fraction to a reaction chamber of a device in the presence of the immobilized ligand for binding interfering cholesterol-containing lipoproteins of another class.

6. A method according to claim 5, wherein the immobilized ligand is an antibody.

7. A method according to claim 6, wherein the immobilized antibody is specific for high density lipoprotein (HDL).

8. A method according to claim 7, wherein the antibody is selected from the class of antibodies consisting of anti-apolipoprotein (apo) A, anti-apoC and anti-apo E.

9. A method according to claim 7, wherein the antibody is anti Apo A1.

10. A method according to claim 7, further comprising the step of removing non-reactant material including Lp(a) from the reaction chamber into a collection chamber by a filtration step.

11. A method according to claim 10, wherein step (iv) further comprises, obtaining Lp(a) in a liquid form that can be concentrated by a predetermined amount.

12. A method according to claim 1, wherein the interfering substances in step (iii) consist of HDL.

13. A method according to claim 1, wherein the volume of the biological fluid sample is less than 10 mls.

14. A method according to claim 1, wherein the volume of the biological fluid sample is 10 mls to 500 mls.

15. A method according to claim 1, wherein the volume of the biological fluid sample is greater than 500 mls.

16. A method of preparing Lp(a) from a biological fluid sample and removing interfering cholesterol-containing lipoprotein and plasma proteins from the preparation, comprising:

(a) preparing Lp(a) according to claim 1;

(b) reacting the Lp(a) of step (iv) with an immobilized ligand wherein the ligand binds a component of the Lp(a) selected from the group consisting of apo(a) protein, apo B100 protein and Lp(a) associated oligosaccharide;

(c) eluting the bound Lp(a) from the ligand; and (d) collecting Lp(a) in a form that is absent biological molecules other than Lp(a).

17. A method according to claim 16, wherein the ligand is selected from the group consisting of lectins, immobilized lysine, fibrin analogues and polyanionic molecules.

18. A method according to claim 16, wherein the ligand is an immune reagent that is specific for at least one of the group consisting of apo(a), Lp(a), apo B100, kringle 4 of Lp(a), kringle 5 of Lp(a), and the protease domain of Lp(a).

19. A method according to claim 16, wherein the immune reagent is selected from the group of antibodies consisting of polyclonal, monoclonal, and recombinant molecules.

20. A method for measuring an amount of one or more isoforms of Lp(a) in a biological fluid containing interfering substances, comprising:

(i) ultracentrifuging the biological fluid in the presence of a salt having a density suitable for separating high density lipoproteins from low density lipoproteins;

(ii) adding the higher density lipoprotein fraction obtained after ultracentrifugation to a reaction chamber of a disposable device, for reacting with an immobilized ligand contained therein, the ligand being capable of selectively binding interfering substances;

(iii) causing substantially all non-reactant material, including the Lp(a) to be removed from the reaction device into a collection chamber through a filter, the ligand-bound interfering substance remaining in the reaction device; and (iv) conducting a clinical assay for Lp(a) on the non-reactant filtrate including Lp(a) in the presence of a standardized reference.

21. A method for analyzing Lp(a) in a clinical sample, comprising:

(a) obtaining a standardized preparation of Lp(a), having a known mass and cholesterol content for acting as a reference for Lp(a) in the sample;

(b) preparing the clinical sample so as to remove interfering substances; and (c) performing an analysis on the clinical sample and the standardized reference to obtain a quantitative value for Lp(a) in the clinical sample.

22. A method according to claim 21, wherein the analysis of step (c) is a cholesterol assay.

23. A method according to claim 21, wherein the analysis of step (c) is a mass assay.

24. A method according to claim 21, wherein the analysis of step (c) is a determination of the isoform of Lp(a).

25. A method for the isolation of Lp(a) that allows for the subsequent determination of the particle isoform, comprising:

(a) separating high density lipoproteins from low density lipoproteins by fractionation;

(b) reacting the high density lipoprotein fraction with a ligand capable of selectively binding related non-Lp(a) substances;

(c) separating the non-reactant fraction from the fraction containing ligand by filtration.

* * * * *